US006580817B2

(12) United States Patent
Badilini

(10) Patent No.: US 6,580,817 B2
(45) Date of Patent: Jun. 17, 2003

(54) APPARATUS AND METHOD FOR READING AND ANALYZING ECG IMAGES

(75) Inventor: Fabio F. Badilini, Montichiari (BS)

(73) Assignee: A.M.P.S., LLC, New York, NY (US)

( * ) Notice: Subject to any disclaimer, the term of this patent is extended or adjusted under 35 U.S.C. 154(b) by 0 days.

(21) Appl. No.: 09/860,097

(22) Filed: May 17, 2001

(65) Prior Publication Data

US 2002/0172404 A1 Nov. 21, 2002

(51) Int. Cl.$^7$ ................................................. G06K 9/00
(52) U.S. Cl. ...................................................... 382/128
(58) Field of Search ................................ 382/128, 130; 600/509, 513, 516, 518, 519, 522

(56) References Cited

U.S. PATENT DOCUMENTS

| | | | |
|---|---|---|---|
| 4,388,759 A | 6/1983 | Orejola | 33/1 C |
| 4,936,022 A | 6/1990 | Grayzel | 3/664 |

OTHER PUBLICATIONS

Morganroth, Joel M.D., et al., "How to Obtain and Analyze Electrocardiograms in Clinical Trials", *Department of Medicine, University of Pennsylvania, Philadelphia, Pennsylvania*, pp. 425–433 (Mar. 30, 1999).

Lepeschkin, Eugene, M.D., et al., "The Measurement of the Q–T Interval of the Electrocardiogram", Circulation, vol. VI, pp. 378–388, (Sep. 1952).

Bland, Martin J., et al., "Statistical Methods for Assessing Agreement Between Two Methods of Clinical Measurement", *The Lancet*, pp. 307–310, (Feb. 8, 1986).

Savelieva, Irina M.D., et al., "Agreement and Reproducibility of Automatic Versus Manual Measurement of QT Interval and QT Dispersion", *Excerpta Medica, Inc.* (1998), pp. 471–536.

Murray, Alan, et al., "Errors in Manual Measurement of QT Intervals", *Br Heart*, vol. 71, pp. 386–390, (1994).

Lawson, W.T., et al., "New Method for Digitization and Computerized Analysis of Paper Recordings of Standard 12–Lead Electrocardiograms", *IEEE—Computers in Cardiology*, pp. 41–44, (1995).

Bhullar, H.K., et al., "A Computer Based System for the Study of QT Intervals", *IEEE—Department of Engineering and Cardiology, University of Leicester, Leicester, UK*, pp. 533–536, (1992).

*Primary Examiner*—Andrew W. Johns
*Assistant Examiner*—Shervin Nakhjavan
(74) *Attorney, Agent, or Firm*—Thomas R. Fitzgerald, Esq.

(57) ABSTRACT

A method of analyzing an electrocardiogram (ECG) paper chart includes the steps of scanning the ECG chart, to thereby create a computer-readable ECG image file representative of the ECG chart, storing the ECG image file in a memory of a computer, opening the ECG image file and displaying on a computer display an ECG plot corresponding to the ECG image file, calibrating the x-axis and y-axis of the displayed ECG plot with an x-axis scale and a y-axis scale, identifying characteristics of the ECG plot by using an input device connected to the computer, and measuring the identified characteristics.

24 Claims, 6 Drawing Sheets

Results 70 200

RR Intervals
- RR1: 885
- RR2: 860
- RR3: 819

QT Intervals
- QT1: 412
- QT2: 419
- QT3: 409

RR: 165
QRS: 107

RRMean: 855

QTMean: 413
QT6: 446
QT1: 435

T-Wave comment: Monophasic ++

T-Wave shape: Normal

OK   Cancel

FIG. 8 file - Blocco note
File  Modifica  Cerca  ?
- Name:     ABAB
- ECGID:    001
- PR:       165
- QRS:      107
- RR1:      885
- RR2:      860
- RR3:      819
- QT1:      412
- QT2:      419
- QT3:      409
- QTMean:   413
- RRMean:   855
- QTc:      446
- QTf:      435
- Comment: Monophasic ++

APPARATUS AND METHOD FOR READING AND ANALYZING ECG IMAGES

FIELD OF THE INVENTION

The present invention relates generally to cardiology, and, more particularly, to an apparatus and method for reading and analyzing electrocardiographic charts, especially electrocardiographic charts recorded on paper.

BACKGROUND OF THE INVENTION

Electrocardiograph (EKG) machines are used as a diagnostic tool in medicine, and measure electrical activity in the heart muscle. After each contraction of the heart, an electrical impulse is generated in the sinoatrial node (SA Node) of the heart. The EKG machine traces the path of the impulse as it spreads though the heart, and produces a graph or trace of the electrical impulses often referred to as an electrocardiogram (ECG). There is a growing need to identify changes that occur in ECGs that are associated with, for example, pharmacological interventions, genotypes and different pathophysiological substrates. For example, one specific need is to determine whether a given compound significantly modulates the repolarization duration process of cardiac beats.

Generally, EKG machines include or are associated with a printing means that produces on paper an ECG chart. Reading and analyzing the paper ECG chart typically requires the use of a ruler or a system of calipers in order to measure and determine certain characteristics of the ECG, such as, for example, time intervals and peak magnitudes. One example of such a caliper system for use in measuring paper ECG charts is described in U.S. Pat. No. 4,388,759, which is herein incorporated by reference. The caliper system described therein is used to determine deflection amplitudes, intervals and frequencies from standard ECG tracings or charts, and consists of two calibrated caliper arms coupled together for rotation about a pivot pin to determine distances between different caliper points. A second example of a caliper system for use in measuring paper ECG charts is described in U.S. Pat. No. 4,936,022, which is also herein incorporated by reference. The caliper system described therein includes a multi-leg caliper device having a plurality of parallel members and pivot points, and is used to measure characteristics of a conventional paper chart ECG by placing several indicia over a suitably calibrated scale and comparing the values on the indicia chart adjacent indicating portions of the multi-leg caliper.

A problem arises when the desired measurement is a time duration between two events. For example, one event may be a peak of one portion of a wave and a valley of another portion. The peak and valley are separated by a substantial vertical distance. An accurate measurement requires projecting the peak and the valley onto the horizontal time axis and then measuring the time between the projected points. The projections must be made to a common horizontal baseline and must be perpendicular thereto. If the baseline is angled from horizontal or if the projection is other than perpendicular, errors in measurement are introduced. Mechanical methods for making such measurements are subject to human and mechanical error.

The above-described and other similar caliper systems are typically restricted to reading only a few of the ECG characteristics of interest. Furthermore, such caliper systems are typically calibrated for use with a paper ECG chart having a predetermined resolution and/or scale, and thus can not be used with other paper charts having a different resolution. Moreover, the caliper-based systems are manual and mechanical in nature, and are thus subject to poor reproducibility and error. Varying resolutions and/or time scales of paper charts and the quality of the ECG tracing on the paper chart are just two examples of factors that have contributed to error and/or poor reproducibility in reading the paper ECG charts. These and other factors which negatively impact the reliability of manually reading paper ECG charts are discussed in greater detail in Savelieva, I., et al., *Agreement and Reproducibility of Automatic versus Manual Measurement of QT Interval and QT Dispersion*, 81 Am. J. Cardiol. 471–477 (1998), and Murray, A., et al., *Errors in Manual Measurement of QT Intervals*, 71 Br. Heart J., 386–390 (1994), each of which are incorporated herein by reference.

Therefore, what is needed in the art is a method of reading and analyzing an ECG chart that is less susceptible to error and has a higher reproducibility.

Furthermore, what is needed in the art is a method of reading and analyzing an ECG chart that is less mechanical in nature.

Still further, what is needed in the art is a method of reading and analyzing an ECG chart that is capable of determining a substantial number of the electrocardiogram characteristics of interest.

Moreover, what is needed in the art is a method of reading and analyzing an ECG chart that is adaptable for use with charts having different resolutions and/or scales.

SUMMARY OF THE INVENTION

The present invention provides an apparatus and method for analyzing an electrocardiogram (ECG) paper chart.

The invention comprises, in one form thereof, a method of analyzing an electrocardiogram (ECG) paper chart that includes the steps of scanning the ECG chart, to thereby create a computer-readable ECG image file representative of the ECG chart, storing the ECG image file in a memory of a computer, opening the ECG image file and displaying on a computer display an ECG plot corresponding to the ECG image file, calibrating the x-axis and y-axis of the displayed ECG plot with an x-axis scale and a y-axis scale, identifying characteristics of the ECG plot by using an input device connected to the computer, and measuring an axial projection of the identified characteristics by connecting a line at any angle between the two points.

An advantage of the present invention is that reading and analyzing the ECG chart is more automated.

Another advantage of the present invention is that a substantial number of the electrocardiogram characteristics of interest are automatically determined or determined with minimal user input.

Yet another advantage of the present invention is that error and reproducibility in reading and analyzing the ECG chart is reduced.

A still further advantage of the present invention is that it is adaptable for use with ECG charts having different resolutions and/or scales.

Other advantages of the present invention will be obvious to one skilled in the art and/or appear hereinafter.

BRIEF DESCRIPTION OF THE DRAWINGS

The above-mentioned and other features and advantages of this invention, and the manner of attaining them, will become appreciated and be more readily understood by reference to the following detailed description of one embodiment of the invention in conjunction with the accompanying drawings, wherein:

FIG. 8 shows a software-based dialog box for use in the method of reading and analyzing an ECG chart of FIG. 3; and FIG. 9 is an example of an exported data file in accordance with the method of reading and analyzing an ECG chart of FIG. 3.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE DRAWINGS

The following terms as used herein are defined as follows. The phrase "reading an ECG" refers to obtaining values for and/or measuring parameters of an ECG. The term "QRS complex" refers to the largest fluctuation of the ECG signal of a duration of approximately 100 milliseconds (mS). Lastly, the term "QT interval" refers to the time interval between the beginning of a QRS complex and the end of the following T wave. The foregoing definitions are more particularly described hereinafter, and will be more readily understood with reference to FIG. 1, wherein an illustrative ECG plot is shown.

Figure 1:
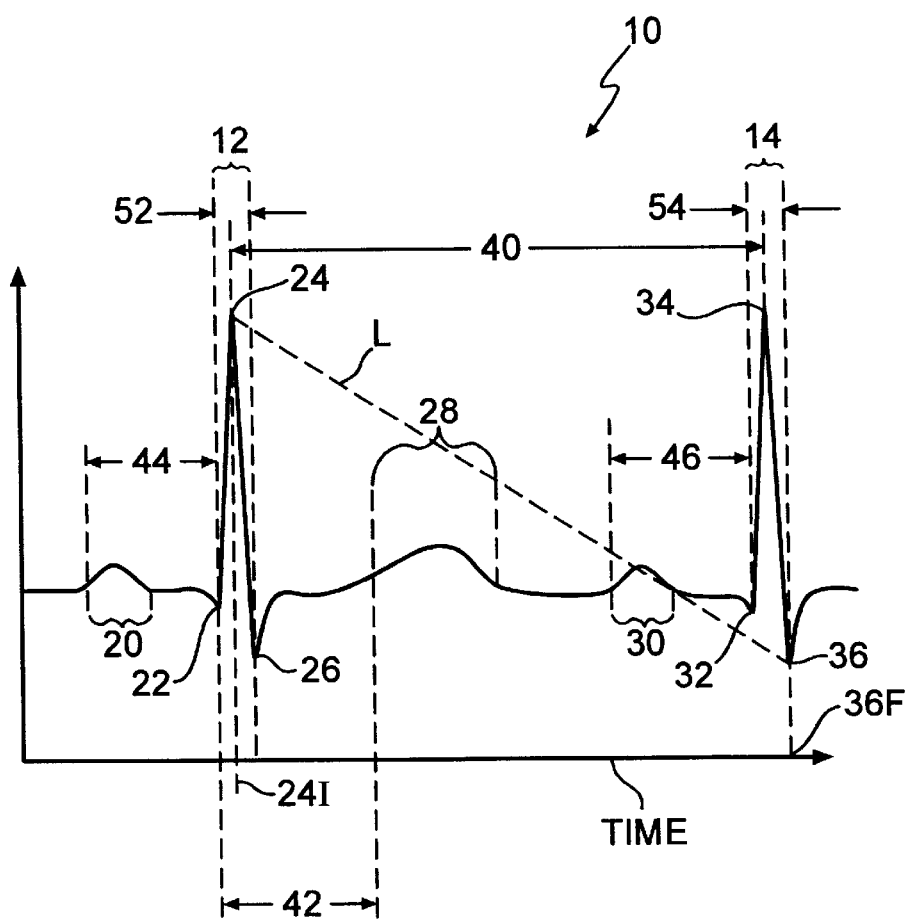
FIG. 1 is an illustrative ECG plot.

Referring now to FIG. 1, ECG plot 10 includes two consecutive QRS complexes, QRS 12 and QRS 14. QRS complex 12 is preceded by P wave 20, and includes a respective Q wave 22, R wave 24, and S wave 26. QRS complex 12 is followed by T wave 28. Similarly, QRS complex 14 is preceded by P wave 30, and includes a respective Q wave 32, R wave 34, and S wave 36. A respective T wave (not shown) follows QRS complex 14. P waves 20, 30 are due to the excitation of the atria. Q waves 22, 32, R waves 24, 34 and S waves 26, 36 result from the excitation of the ventricles. T wave 28 is due to the ventricles returning to electrical steady state (repolarization of the ventricles).

RR interval 40 is the time interval between R wave 24 and R wave 34, and provides a direct estimate of instantaneous, rather than averaged, heart rate. QT interval 42 is the time interval between the onset of Q wave 22 and end or offset of T wave 28, and it is useful in assessing the time between ventricular excitation (i.e., polarization and/or contraction) and ventricular return to steady state (i.e., repolarization and/or decontraction).

Further of note in FIG. 1 are PR intervals 44, 46 and QRS intervals 52, 54. PR intervals 44, 46 each reflect the time between a respective excitation of the atria and excitation of the ventricles. QRS intervals 52, 54 each reflect the time interval of a complete excitation of the ventricular muscle.

At rest the heart is neutral and has a nominal zero voltage. However, normal ECGs have a wandering DC level. In other words, each cycle of the PQRST wave does not return to the same absolute value of zero. Nevertheless, the region of the wave following the T portion, and the region between the P wave and following QRS wave, are considered neutral, and sequential corresponding portions can be used to establish a baseline of zero volts. For purposes of illustration, assume that a doctor wanted to know the time between the R peak 24 of the first ECG and the Q valley 36 of the second one. Using prior art techniques, the two points would be projected onto a baseline Time as points 24I and 36F and the distance between the two could be measured with a ruler.

In contrast, the invention allows the user to place a first end point of a line L on the peak 24 and a second end point on the valley 36 to thereby measure the interval of interest. First, the horizontal axis is scaled. The scale is selected from data taken with the ECG. These are known values of so many millivolts or seconds per division on the graph paper. The scale for the x-axis is created by drawing a conventional horizontal line between two major divisions on the bit mapped image and entering the time represented by the distance. The y-axis is similarly scaled. With the bitmapped imaged thus scaled, the computer program automatically finds the length of the projection of the end points on the respective horizontal and vertical axes. Since the image is bitmapped, the computer counts the horizontal and vertical pixels located between the two end points and displays the results. Thus, the angle of the line between the two points is determined. In order to precisely place the end points of the line, the user may magnify or zoom in on the images and place the end points on the magnified peak or valley. Of course, other methods of finding the axial projections could be used, including and not limited to solving the Pythagorean theorem and using trigonometry.

Figure 2:
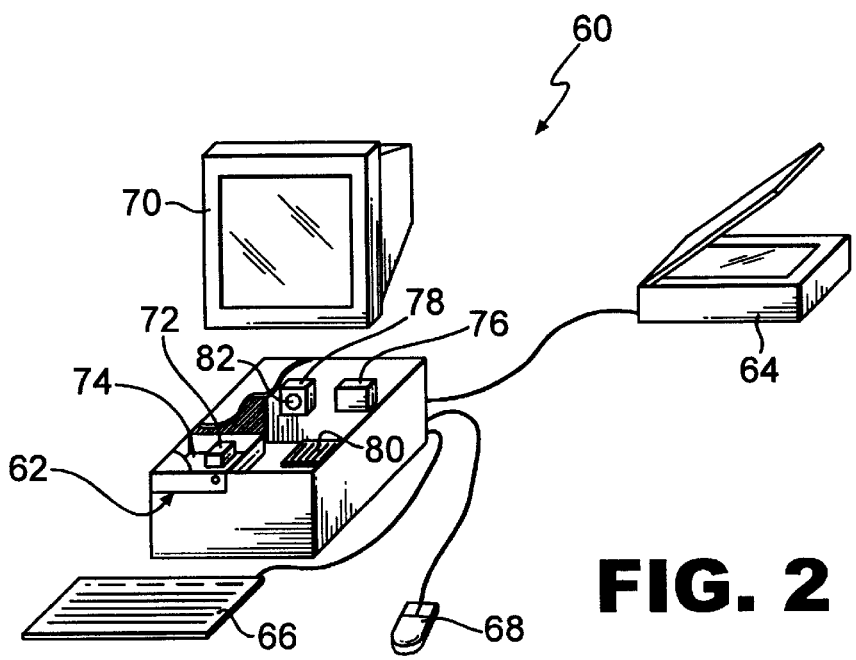
FIG. 2 shows one embodiment of an apparatus for reading and analyzing an ECG chart of the present invention.

Referring now to FIG. 2, one embodiment of an apparatus for reading and analyzing an ECG plot is shown. ECG analyzing and measurement system 60 includes computer 62, such as, for example, a personal computer, and optical scanner 64.

Personal computer 62 includes keyboard 66, mouse 68 and display 70. Personal computer 62 further includes application software 72, which will be more particularly described hereinafter, that is stored in storage device 74, such as, for example, a hard drive, floppy drive or compact disk drive, connected to personal computer 62. Personal computer 62 further includes read only memory (ROM) 76 and random access memory (RAM) 78. The basic functions of personal computer 62 are controlled by operating system 80, such as, for example, a version of the WINDOWS operating system.

Optical scanner 64 is electrically connected to computer 62, such as, for example, via an input/output port (not shown). Optical scanner 64 is a commercially available scanner such as those sold for use with personal computers as peripheral equipment.

Figure 3:
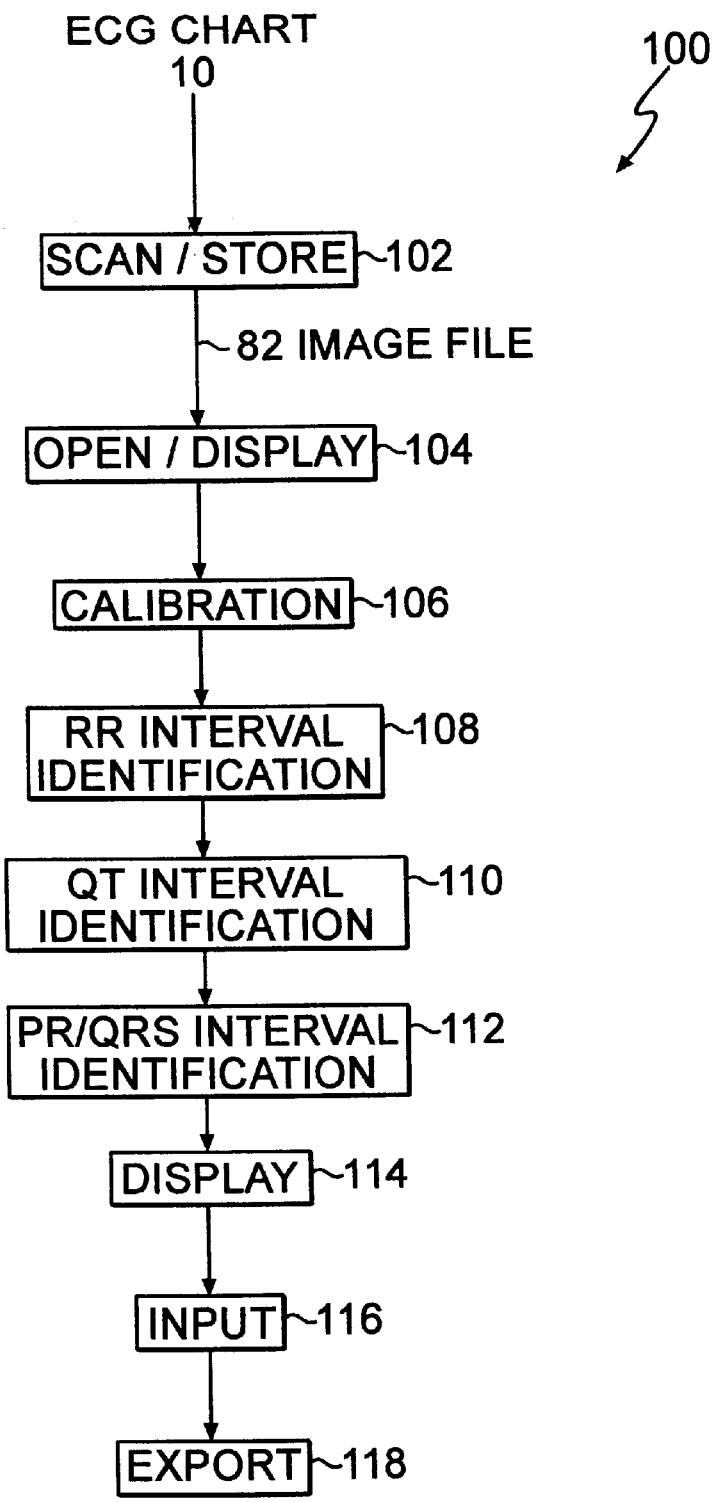
FIG. 3 is a flow chart illustrating one embodiment of a method for reading and analyzing an ECG chart of the present invention.

Referring now to FIG. 3, the process steps of one embodiment of the method of reading and analyzing an ECG of the present invention are shown. ECG reading and analyzing method 100 is performed by EGR reading system 60 running application software 72. As will be more particularly described hereinafter, ECG reading and analyzing method 100 includes scanning step 102, file opening step 104, calibrating step 106, RR interval identification step 108, QT interval identification step 110, PR/QRS interval identification step 112, display step 114, input step 116 and exporting step 118.

Scanning step 102 of method 100 includes scanning ECG plot 10 with scanner 64. ECG plot 10 is placed on the scanning bed (not shown) of optical scanner 64. ECG plot 10 is a conventional plot with known scales for its horizontal and vertical axes. The image of the plot is typically a light gray grid pattern that bears a dark line image of an ECG wave. Computer 62 controls the operation of scanner 64 through operating system 80 or other software, and controls the execution of application software 72 and, thus, method 100. Scanning step 102 creates image file 82, and stores image file 82 as a computer-readable graphics file in RAM 78 or storage device 74 of computer 62. After scanning, the bitmapped image 82 comprises a plurality of pixels. All pixels are square and have the same dimensions. Image file 82 is a graphics file of a predetermined or user selected format, such as, for example, a bitmap file format or a Joint Photographic Experts Group (JPEG) file format. Scanning step 102 scans ECG plot 10 at a resolution, such as, for example, approximately 100 to 200 dots per inch (dpi), or higher, depending on the capabilities of scanner 64 and any user, software or apparatus-imposed limitations on file size. Image file 82 is then opened and a representation thereof displayed on computer display 70 by file open step 104.

Figure 4:
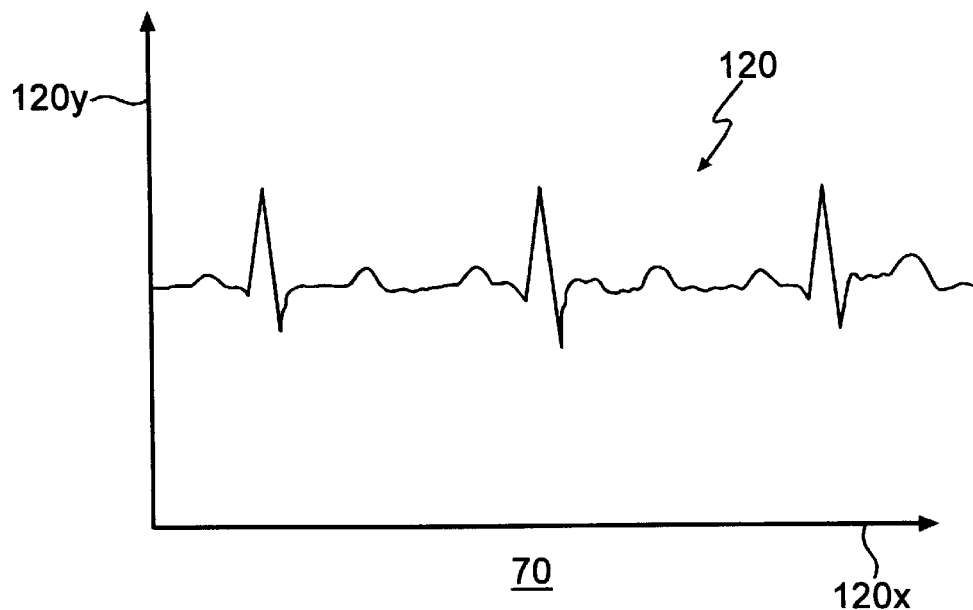
FIG. 4 is a bitmapped image of an ECG chart displayed in accordance with the method of FIG. 3.

Referring now to FIG. 4, a representation of a scanned ECG wave is shown. Scanned ECG wave 120 is displayed on computer display 70, and includes x-axis 120x and y-axis 120y. Scanned ECG wave 120 is the result of scanning step 102, saving step 103 and file open step 104, and is a visual representation of image file 82. File open step 104 includes selecting and opening image file 82, and the display of image file 82 on computer display 70 as scanned ECG wave 120.

Figure 5:
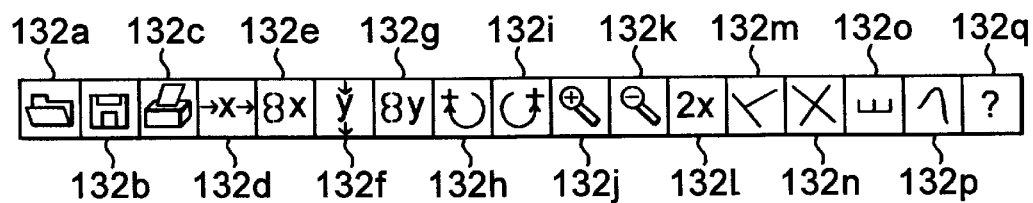
FIG. 5 is a display of a software-based toolbar for reading and analyzing an ECG plot in accordance with the method of FIG. 3.
Figure 5:
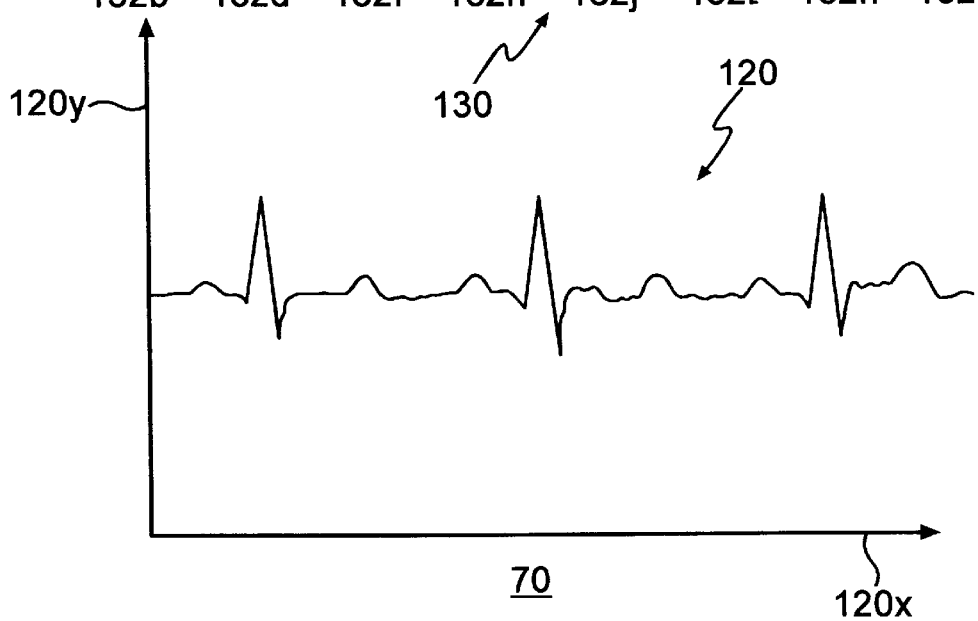

Calibration step 106 includes the addition by a user of a scale, typically time, for x-axis 120x and a scale, typically voltage, for y-axis 120y to scanned ECG wave 120. More particularly, and with reference to FIG. 5, calibration step 106 enables a user, through the use of one or both of mouse 68 and keyboard 66, to access tool bar 130 of application software 72 that is displayed on computer display 70 and includes a plurality of buttons 132a–132q. Each of buttons 132a–132q includes an icon (not referenced) representative of the functions performed by that button. By positioning mouse 68 upon an icon or button, or selecting the appropriate icon with the keys of keyboard 66, button 132e is activated to enable the user to assign a scale or time to x-axis 120x, or button 132f is activated to enable the user to assign a scale or voltage to y-axis 120y of scanned ECG wave 120.

The toolbar 130 includes conventional Windows icons on buttons 132a–c for opening files, saving files and printing, respectively. Button 132d selects and toggles the x-scale function and button 132e confirms and locks the scale. Button 132f and 132g perform corresponding functions for the y-axis. Buttons 132h–l perform the functions of rotating the image clockwise and counter-clockwise, and for enlarging, reducing and doubling the size of the image, respectively. Button 132m is used to select a line that is drawn on the image. Button 132n refreshes the image by saving the line data but removing the display of drawn lines from the image. Button 132o is clicked to confirm the tangent made from several samples and icon 132p is used when a single tangent is drawn. Button 132q is an icon that brings up a help screen with one or more menu choices to assist the user.

The user, after activating toolbar button 132d, is prompted by application software 72 to scale a portion of or the entire x-axis 120x of scanned ECG wave 120 by drawing a line generally parallel to x-axis 120x. The user is prompted by application software 72 to first click mouse 68 at a selected first point, such as, for example, the origin, of scanned ECG wave 120 and then at a second point spaced in the general direction of x-axis 120x from the first selected point. Application software 72 then prompts the user to enter a time interval or duration that corresponds to the length of the line drawn. The requested time interval is entered by the user via either keyboard 66 or by selecting the appropriate number from a pop-up list via mouse 68. Thus, the portion of x-axis 120x of ECG wave 120 corresponding to the line drawn in the general direction of x-axis 120x is assigned a time parameter or scale by application software 72. Alternatively, application software 72 is configured with a default time scale, such as, for example 200 mS, and the user is instructed to draw a line generally parallel with x-axis 120x and extending through a portion of scanned ECG wave 120 that corresponds to the default time scale. In either embodiment, once a time scale has been assigned to at least a portion of x-axis 120x of scanned ECG wave 60, application software 72 then accordingly scales the entire x-axis 120x of scanned ECG wave 120.

Y-axis 120y or voltage axis is similarly provided with a scale. The user again accesses tool bar 130 of application software 72, which is displayed on display 70. By operating the preferred input device, button 132f is activated to enable the user assign a scale to y-axis 120y of scanned ECG wave 120. After activating toolbar button 132f, the user is prompted by application software 72 to scale a portion of or the entire y-axis 120y of scanned ECG wave 120 by drawing a line generally parallel with y-axis 120y by clicking the mouse at a first selected point, such as, for example, the origin, of scanned ECG wave 120 and then at a second point spaced from the first selected point in the general direction of y-axis 120y. Application software 72 then prompts the user, in a manner similar to that described above for scaling x-axis 120x, to enter a voltage interval corresponding to the length of the line drawn. Thus, the portion of y-axis 120y of ECG wave 120 corresponding to the line drawn generally parallel to y-axis 120y is assigned a voltage parameter or scale. Alternatively, application software 72 is configured with a default voltage scale, such as, for example 1 milliVolt (mV), and the user is instructed to draw a line that is generally parallel to y-axis 120y and which extends through a portion of scanned ECG wave 120 that corresponds to the default voltage scale. In either embodiment, once a voltage scale has been assigned to at least a portion of y-axis 120y of scanned ECG wave 120, application software 72 then accordingly scales the entire y-axis 120y of scanned ECG wave 120.

After the image is scaled, any horizontal or vertical distance between two points is precisely measured without having to adjust the line to be a horizontal projection of the two points. The program next provides for taking three RR intervals measurements 108, followed by three QT measurements 110 and finally the PR and QRS intervals. Since the RR and QT intervals are highly variable, it is conventional to take three or more measurements and then take an average of them. The PR and QRS intervals are less variable and one measurement is usually sufficient for ordinary diagnostic purposes.

Application software 72 further provides for the identification and/or labeling of the characteristics of scanned ECG wave 120, and subsequent analysis of the characteristics and parameters of scanned ECG wave 120. More particularly, the characteristics of scanned ECG wave 120, such as, for example, a QRS interval, an RR interval, a QT interval, or other desired characteristics and/or intervals, are identified by selecting a desired portion of scanned ECG wave 120 in RR interval identifying step 108, QT interval identifying step 110, and PR/QRS interval identifying step 112.

Figure 6:
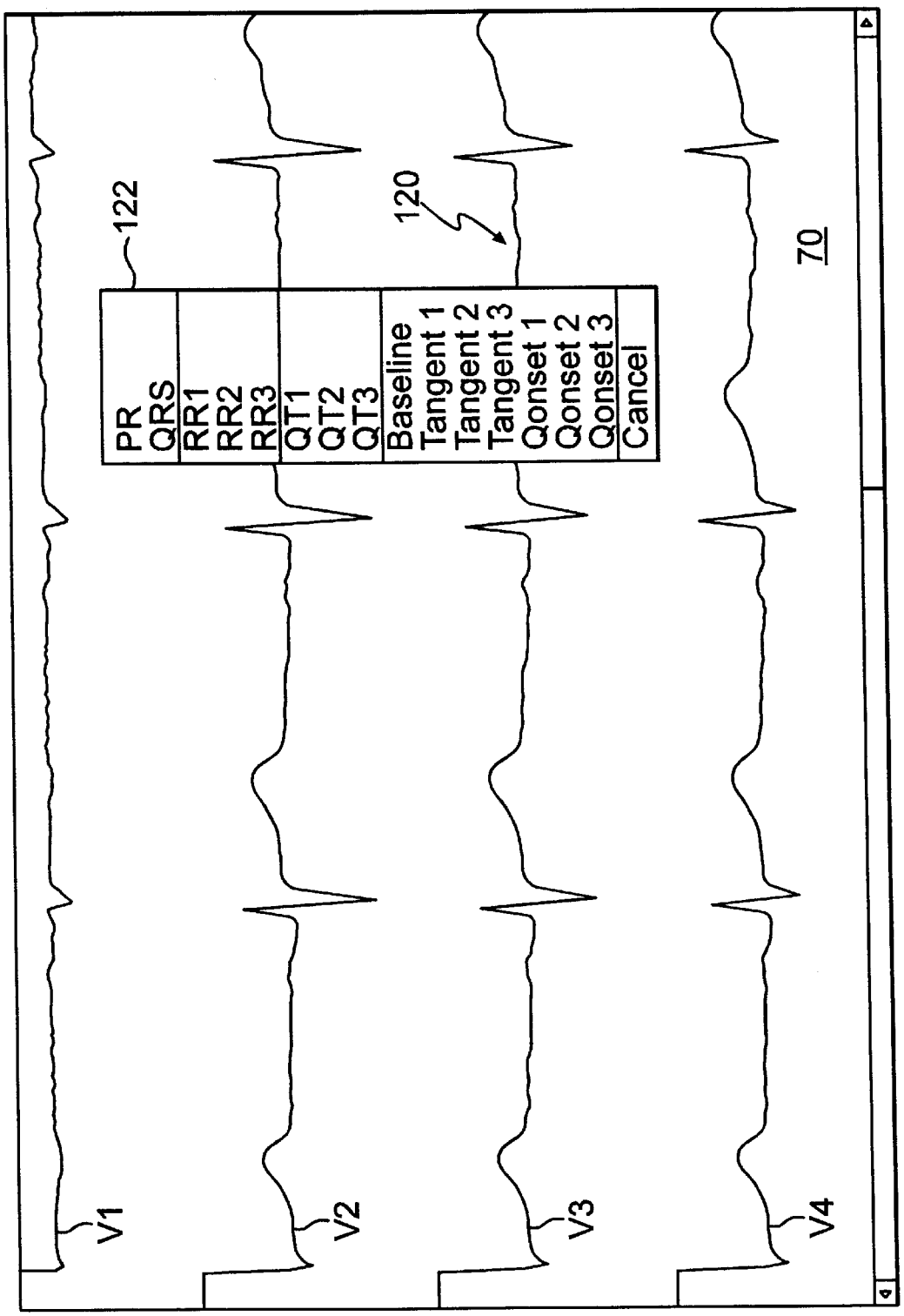
FIG. 6 shows a pop-up contextual menu for reading and analyzing an ECG plot in accordance with the method of FIG. 3.

In RR interval identifying step 108, QT interval identifying step 110 and PR/QRS interval identifying step 112 (collectively referred to hereinafter as identifying steps 108–112), the user selects a desired portion of scanned ECG wave 120 to be identified by clicking or activating a button of mouse 68 at the beginning of the characteristic or interval to be identified and/or labeled. A first click sets one end point of a line, e.g. at the first R peak 24. The user holds the mouse button down and drags mouse 68 to the end of the interval or characteristic of interest, e.g. the second R peak 34. As the user drags mouse 68, application software 72 highlights the portion of scanned ECG wave 120 thus far selected. The user drags mouse 68 to the end of the desired characteristic of interest, and releases the mouse button. Upon release of the mouse button, application software 72 activates pop-up menu 122 (FIG. 6), which includes a list of typical characteristics from which the user selects via mouse 68 or keyboard 66 the item that corresponds to the portion of scanned ECG wave 120 previously selected. Thus, the selected portion of scanned ECG wave 120 is labeled and/or identified. In the example given above, the user has selected the first of three RR intervals.

It is typical when analyzing an ECG plot to measure a maximum of three RR intervals and three associated QT intervals. Furthermore, it is typical to measure a single PR and a single QRS interval. Thus, identifying steps 108–112 of application software 72 include default settings which correspond to the typical intervals and the typical quantities thereof. However, through a separate set of user accessible menus, the default settings of application software 72 are changed by the user.

In addition to identifying and/or labeling characteristics of scanned ECG wave 120 by selecting an interval thereof that corresponds to the desired characteristic in identifying steps 108–112, application software 72 enables a user to perform various additional measurement and/or identifying functions and techniques. Such additional techniques are useful in identifying and/or measuring characteristics of an ECG plot that require baseline identification.

The baseline of an ECG plot, also referred to as the isoelectric line, is theoretically the zero volt line or level. However, the baseline of an actual non-theoretical ECG plot does not necessarily correspond to and is typically not coincident with the actual zero volt line. Thus, it is often necessary to estimate the baseline of an ECG plot. The baseline is typically estimated as the line between two consecutive isoelectric points inside a PR interval of the EGG plot. During a PR interval the myocardium is generally assumed to be electrically neutral, and thus the two consecutive points are chosen to be within a PR interval.

Baseline identification is critical to the identification and measurement of various parameters of an ECG plot, such as, for example, QT intervals. Generally, the end of a QT interval is defined as the return of the T wave to the baseline of the ECG signal. Thus, in order to properly measure and identify a QT interval, the baseline of the ECG plot must be identified. Conventionally, measuring and/or identifying a QT interval has been performed by what is referred to as the tangent approach. Generally, the tangent approach involves establishing a baseline for the ECG plot, drawing a tangent line that is tangential to the negative sloped or decreasing portion of the T wave, and drawing a line that indicates the onset of a QRS interval with which the T wave is associated. The distance between the QRS onset and the point at which the tangent line intersects the baseline determines the QT interval.

When performed manually and directly on paper ECG plots, the tangent approach is rather tedious and time consuming. Further, mistakes in the manual practice of the tangent approach are likely to require numerous erasures and thereby create a confusing ECG plot subject to interpretational errors. The method of the present invention enables a user to quickly and easily practice the tangent approach and measure a QT interval by facilitating the identification of the ECG plot baseline, the drawing of tangent lines, and the indication of the onset of associated QRS intervals as more particularly described hereinafter.

Figure 7:
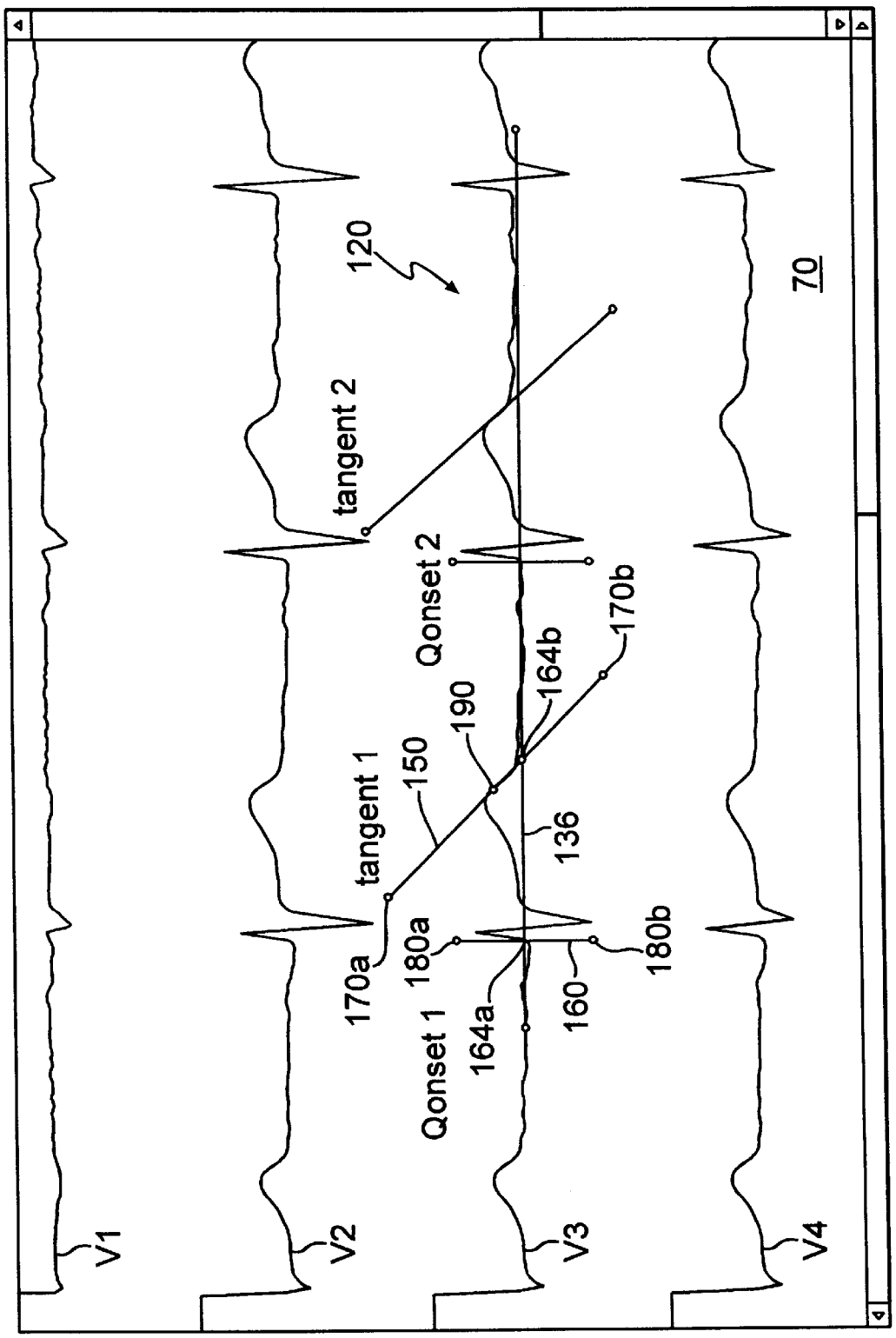
FIG. 7 illustrates the step of identifying characteristics of an ECG plot in accordance with the method of FIG. 3.

Application software 72 enables a user to measure a QT interval by practicing the tangent approach in a manner that substantially reduces the problems associated with the manual performance thereof upon a paper ECG plot. In order to do so, the user first selects from menu 122 of application software 72 the appropriate Tangent option (i.e., Tangent 1, Tangent 2 or Tangent 3). More particularly, and with reference to FIG. 7, the user selects from menu 122 the Baseline option and draws on scanned ECG plot 120 a single baseline 136 according to a click and drag method that is substantially similar to the method described above in regard to calibrating step 106 (i.e., the scaling of x and y axes 120$x$, 120$y$, respectively), whereby the user clicks a button of mouse 68 over a starting point for baseline 136 and then drags mouse 68 to and releases the mouse button at an ending point for baseline 136. The baseline 136 is constructed with one end point at a first QT region and the second end point at the second or third QT region.

With baseline 136 thus established, the user selects from menu 122 of application software 72 the appropriate Tangent option and draws a tangent line. The tangent line is tangent to a selected or desired negative-sloped portion of the T wave associated with the QT interval to be measured. The method by which the tangent line is drawn is substantially similar to the method described above in regard to calibrating step 106, whereby the user clicks a button of mouse 68 on a starting point for tangent line and then drags mouse 68 to and releases the mouse button at an ending point for tangent line. Tangent line 150 is thus drawn and appears on computer display 70. Tangent line 150 may be rotated about either end point and may be transversely moved to other parallel locations in order to precisely position the tangent line on the declining T slope, as will be more particularly described hereinafter.

Similarly, the QRS onsets of scanned ECG plot 120 are identified by the user selecting from menu 122 of application software 72 the appropriate Qonset command, i.e., Qonset 1, Qonset 2, or Qonset 3, which permit the user to identify the onset of a QRS interval. After selecting this option, the user is prompted to position mouse 68 over the beginning of a Q wave and click a mouse button to thereby establish the onset of a QRS interval. Application software 72 then generates and displays Q line 160 which corresponds to the onset of a QRS interval associated with the selected Q wave.

QT intervals are calculated by the user activating button 132$p$ of toolbar 130 by appropriate input via either keyboard 66 or mouse 68. Application software 72 calculates the distance between the intersection of Q line 160 with baseline 136, which point is designated as intersection point 164a in FIG. 7, and the intersection of tangent line 150 with baseline 136, which point is designated as intersection point 164b in FIG. 7. This distance corresponds to the QT interval.

Each of tangent line 150 and Q line 160 include respective translational tools 170a, 170b and 180a, 180b, graphically represented on scanned ECG plot 120 as square boxes disposed at the end of tangent line 150 and Q line 160. Further, tangent line 150 includes rotational tool 190, which is represented on scanned ECG plot 120 as a round box near the midpoint of tangent line 150. Application software 72 enables a user to select one of translational tools 170a, 170b and 180a, 180b to translate, i.e., position relative to x-axis 120x, a corresponding tangent line 150 and Q line 160, respectively. Similarly, application software 72 enables a user to select rotational tool 190 to rotate, i.e., in a clockwise or counter-clockwise direction, tangent line 150. Thus, the user of application software 72 is able to easily and quickly manipulate the horizontal position and angle of tangent lines and the horizontal position of Q lines in order to identify and measure QT intervals in a more efficient and less error prone manner than when manually performing the tangent method on a paper ECG plot.

Alternatively, application software 72 is configured to perform the tangent method by establishing a separate baseline for each respective QT interval to be measured. This embodiment is particularly useful when the scanned ECG chart which is to be analyzed has a poorly-defined or difficult to determine overall baseline. According to this embodiment, a user selects from a menu of application software 72 an option to determine individual baselines, rather than the default singular baseline (as described above), for each QT interval. Then, the process of establishing baseline 136, as described above, is repeated to thereby establish a respective baseline for each QT interval to be measured.

In addition to the analysis and measurements described above, additional measurements and parameters of scanned ECG plot 120, such as, for example, average RR intervals, an average QT interval of the measured QT intervals, the QT interval corrected by the Bazett formula, and the QT interval as corrected by the Fridericia formula, are automatically determined by application software 72 performing the method of the present invention. As shown in FIG. 8, these quantities are displayed in dialog box 200, which displays on display 70 a list of the aforementioned and other measurements and parameters of interest.

Application software 72 includes exporting step 118, which exports and saves in a file the measured, calculated and qualitative parameters of the analyzed ECG wave on a selected one or both of storage device 74 and RAM 78. Referring now to FIG. 9, file 220 contains the parameters and measurements shown in FIG. 7, and is of a standard and widely-used file format, such as, for example, the American Standard Code for Information Interchange (ASCII) file format. File 220 includes a list of parameters or measurement names, such as QRS, and a value associated with each of the parameters. However, it is to be understood that file 220 can be alternately configured, such as, for example, as a text file or other file format. Furthermore, it is to be understood that the data contained in file 220 can be alternately arranged, such as, for example, organized into a form that resembles typical sheets used in clinical trials or in a clinical report form format. Still further, file 220 can be alternately configured to include additional parameters and measurements, and to include qualitative parameters based upon the interpretation of scanned ECG plot 120, such as, for example, comments on the quality of the ECG chart, indications of morphologies, etc. Moreover, file 220 can be alternately configured in a format compatible for use with any number of commercially available spreadsheet programs to thereby enable a user to graph, sort and perform further analysis of the data contained therein.

Alternatively, file 220 is configured in an application-specific format readable by application software 72, and includes a representation of the analyzed ECG wave, such as, for example, in a bitmap format that includes the wave itself, and data corresponding to any tangent lines, Q lines, QRS intervals, etc. Furthermore, file 220 alternatively includes, in addition to the representation of the analyzed ECG wave, the measured and/or calculated parameters.

In the embodiments shown, the method of the present invention is described in connection with the measurement and analysis of an ECG plot. However, it is to be understood that the method of the present invention can be applied to other types of electrophysiologic signals, plots, graphs, etc.

In the embodiment shown, scanning step 102 is controlled by operating system 80 of computer 62. However, it is to be understood that application software 72 can be alternately configured, such as, for example, to control scanner 64 and perform scanning step 102. Furthermore, it is to be understood that application software 72 can be alternately configured to read and digitize output data directly from an EKG machine and display a scanned representation of the EKG machine output data, rather than scanning a paper ECG chart.

While this invention has been described as having a preferred design, the present invention can be further modified within the spirit and scope of this disclosure. This application is therefore intended to cover any variations, uses, or adaptations of the present invention using the general principles disclosed herein. Further, this application is intended to cover such departures from the present disclosure as come within the known or customary practice in the art to which this invention pertains and which fall within the limits of the appended claims.

What is claimed:

1. A computerized method of analyzing an electrocardiogram (ECG) paper chaff, comprising the steps of:

scanning the EGG chart to thereby create a computer-readable EGG image file representative of the EGG chart;

storing said EGG image file in a memory of a computer; opening said EGG image file;

displaying an EGG plot of said ECG image file on a display of the computer; calibrating an x-axis and a y-axis of said EGG plot;

identifying one or more features on said EGG plot by using at least one input device connected to the computer;

drawing a feature line with a first end point at one feature and second end point at a second feature; and automatically finding the distance between the two end points as projected upon one or both fixes of said EGG plot.

2. The method of claim 1, wherein said scanning step comprises scanning the ECG chart with an optical scanner.

3. The method of claim 1, wherein said storing step comprises storing said ECG image file in a memory of the computer, said memory comprising one of a random access memory, a read only memory, a hard disk and a floppy disk.

4. The method of claim 1, wherein said calibrating step comprises:

scaling the x-axis of said ECG plot; and scaling the y-axis of said ECG plot.

5. The method of claim 4, wherein each of said scaling steps comprise: accessing a tool bar displayed on the computer display;

selecting a button of said toolbar corresponding to one of the x-axis and the y-axis of said EGG plot to thereby select one of the x-axis and y-axis for calibration; and drawing a calibration line for one or both axes and assigning a calibrated scale to the length of the line and to the axes.

6. The method of claim 5, wherein said drawing step comprises:

drawing a calibration line of a predetermined length, said predetermined length corresponding to a default value; and assigning said default value to a portion of the selected one of the x-axis and the y-axis, said portion having a portion length equal to said predetermined length.

7. The method of claim 6, comprising the further step of calculating a magnitude of a projection of said feature line onto one of the calibrated axes, said projection being substantially parallel to the selected axis, said magnitude corresponding to the product of the scale of the axis and the length of the projected line.

8. The method of claim 5, further comprising the step of inputting a value corresponding to a projection of said calibration line, said projection being substantially parallel to the selected one of the x-axis and the y-axis, said value being assigned to an equal length of the selected one of the x-axis and the y-axis.

9. The method of claim 1, wherein said identifying step comprises selecting with an input device at least one of an RR interval, a QT interval, a PR interval, a QRS interval, a baseline, a tangent line, and an onset of a QRS interval.

10. The method of claim 9, wherein said identifying step further comprises selecting a first point on the ECG plot that corresponds to a beginning of a selected one of an RR interval, a QT interval, a PR interval, a QRS interval, a baseline, a tangent line, and an onset of a QRS interval, and selecting with an input device a second point on the ECG plot that corresponds to an end of the selected one of an RR interval, a QT interval, a PR interval a QRS interval, a baseline, a tangent line, and an onset of a QRS interval.

11. The method of claim 10, further comprising the step of labeling the selected one of an RR interval, a QT interval and a QRS interval, a baseline and a tangent line.

12. The method of claim 11, wherein said labeling step comprises selecting with an input device a label from a menu displayed on the display of the computer, said label corresponding to the selected one of an RR interval, a QT interval, a PR interval, a QRS interval, a baseline, a tangent line, and an onset of a QRS interval.

13. The method of claim 1, wherein said measuring step comprises calculating a duration of at least one of an RR interval, a QT interval, a PR interval and a QRS interval identified in said identifying step.

14. The method of claim 1, comprising the further step of calculating and displaying a baseline of said ECG plot.

15. The method of claim 14, wherein said calculating and displaying a baseline step is performed separately for each QRS interval of the ECG plot to thereby establish a respective baseline for each QRS interval.

16. The method of claim 1, comprising the further step of calculating with the tangent method a QT interval identified in said identifying step.

17. The method of claim 16, wherein said calculating with the tangent method step comprises:

accessing a tool bar displayed on the computer display;

selecting a button of said toolbar corresponding to said calculating with the tangent method step; and displaying on the display the calculated QT interval.

18. The method of claim 17, wherein each of said calculating an average of the RR intervals and said calculating an average QT interval comprises selecting a corresponding command form a dialog box displayed on the display.

19. The method of claim 18, wherein said exporting step further comprises storing data representative of the ECG plot in said data file, storing data representative of said calibrating step, and storing data representative off said identifying step, to thereby enable subsequent display and analysis of the analyzed ECG plot.

20. The method of claim 1, comprising the further steps of:

calculating an average of the RR intervals identified in said identifying step and measured in said measuring step; and calculating an average QT interval of the QT intervals identified in said identifying step and measured in said measuring step.

21. The method of claim 1, comprising the further step of:

exporting the results of said measuring step to a computer-readable file.

22. A computerized method of analyzing an electrocardiogram (ECG) paper chart, comprising the steps of:

scanning the ECG chart to thereby create a computer-readable ECG image file representative of the ECG chart;

storing said ECG image file in a memory of a computer;

opening said ECG image file;

displaying an ECG plot of said ECG image file on a display of the computer;

scaling each of an x-axis and a y-axis of said ECG plot by accessing a toll bar displayed on the computer display, selecting a button of said toolbar corresponding to one of the x-axis and the y-axis to thereby select one of the x-axis and y-axis for calibration, and drawing a line generally parallel with the selected one of the x-axis and the y-axis of said ECG plot;

identifying characteristics of said ECG plot by selecting with an input device connected to the computer at least one of an RR interval, a QT interval, a PR interval, a QRS interval, a baseline, a tangent line, and an onset of a QRS interval; and drawing a feature line between two feature points and finding a projected axial distance between the two feature points by calculating a duration each of the RR intervals, QT intervals, PR intervals and QRS intervals identified in said identifying step.

23. The system of claim 22, wherein said application software includes:

a scanning module enabling a user to control said scanner to scan the ECG chart and thereby create a computer-readable ECG image file representative of the ECG chart;

a storing module saving said ECG image file in a memory of a computer;

a file open module to enable a user to open said ECG image file;

a display module displaying an ECG plot of said ECG image file on a display of the computer;

a calibrating module to calibrate an x-axis and a y-axis of said ECG plot;

an identifying module to identify characteristics of said ECG plot by using at least one input device connected to the computer;

a measuring module measuring said identified characteristics; and a calculating module calculating parameters of said ECG plot based upon said identified characteristics.

24. A system for analyzing an EGG paper chart, comprising: a computer having a display, keyboard and mouse;

a scanner electrically interconnected with said computer; and application software stored in a memory of said computer and being executable thereon, said application software configured for displaying, identifying, measuring and calculating characteristics of an image file representing said EGG chart, and drawing a feature line between two characteristics, said image file created by scanning with said scanner the ECG chart.

* * * * *

UNITED STATES PATENT AND TRADEMARK OFFICE
CERTIFICATE OF CORRECTION

PATENT NO.    : 6,580,817 B2
DATED         : June 17, 2003
INVENTOR(S)   : Fabio F. Badilini It is certified that error appears in the above-identified patent and that said Letters Patent is hereby corrected as shown below:

Column 10,
Line 44, delete the word "chaff" and insert the word -- chart --
Line 60, delete the word "fixes" and insert the word -- axes --

Signed and Sealed this

Sixteenth Day of September, 2003

JAMES E. ROGAN
*Director of the United States Patent and Trademark Office*